United States Patent [19]

Boroschewski et al.

[11] 4,453,973
[45] Jun. 12, 1984

[54] CARBAMINIC ACID ESTERS WITH HERBICIDAL PROPERTIES

[75] Inventors: Gerhard Boroschewski; Ludwig Nüsslein; Friedrich Arndt, all of Berlin, Fed. Rep. of Germany

[73] Assignee: Schering Aktiengesellschaft, Berlin and Bergkamen, Fed. Rep. of Germany

[21] Appl. No.: 337,004

[22] Filed: Jan. 4, 1982

Related U.S. Application Data

[62] Division of Ser. No. 87,637, Oct. 23, 1979, Pat. No. 4,344,790.

[30] Foreign Application Priority Data

Oct. 11, 1978 [DE] Fed. Rep. of Germany ....... 2844806

[51] Int. Cl.³ .................. A01N 37/46; C07C 125/067
[52] U.S. Cl. .................................. 71/105; 260/465 D
[58] Field of Search ............... 260/465 D; 560/29, 31, 560/32; 549/452; 71/105, 111

[56] References Cited

U.S. PATENT DOCUMENTS 3,792,994  2/1974  Baker et al. .............. 71/67
3,836,564  9/1974  Baker et al. .............. 560/29
3,836,570  9/1974  Szabo ....................... 560/29
3,872,157  3/1975  Brokke et al. ............ 560/29
3,898,273  8/1975  Baker et al. .............. 560/29
3,979,202  9/1976  Olin et al. ................ 560/29

Primary Examiner—Dolph H. Torrence
Attorney, Agent, or Firm—Michael J. Striker

[57] ABSTRACT

Novel carbaminic acid phenyl esters of the general formula

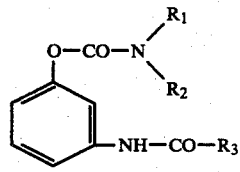

are described, in which
  $R_1$ is $C_1$-$C_2$-alkoxy-$C_1$-$C_2$-alkyl, di-$C_1$-$C_2$-alkoxy-$C_1$-$C_2$-alkyl, cyano-$C_1$-$C_2$-alkyl, halogen-$C_1$-$C_2$-alkyl, phenyl-$C_1$-$C_2$-alkyl, 1,3-dioxolan-2-yl-methyl, 2-methyl-1,3-dioxolan-4-yl-methyl, 2,2-dimethyl-1,3-dioxolan-4-yl-methyl or aminocarbonylmethyl;
  $R_2$ is phenyl optionally mono- or disubstituted by one or more substituents selected from the group consisting of halogen, methyl and methoxy; and
  $R_3$ is $C_1$-$C_8$ alkyl, $C_2$-$C_8$ alkenyl, cyclopropyl or trichloromethyl, or $R_1$ is methyl or ethyl, $R_2$ is α-cyanobenzyl or 1-cyano-2-phenylethyl and $R_3$ is ethyl.

23 Claims, No Drawings

CARBAMINIC ACID ESTERS WITH HERBICIDAL PROPERTIES

This is a division of application Ser. No. 087,637, filed Oct. 23, 1979, now U.S. Pat. No. 4,344,790.

The invention concerns novel carbaminic acid phenyl esters, methods for the preparation of these compounds as well as herbicidal compositions containing at least one of these compounds.

Herbicidal 3—(carbamoyloxy)—anilides are already known (BE-PS 686 239). It is an object of the invention to provide active agents with exceptional herbicidal properties. This object is achieved through a composition containing at least one compound of the general formula

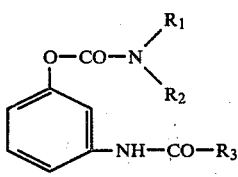

in which $R_1$ $C_1$-$C_2$-alkoxy-$C_1$-$C_2$-alkyl, di-$C_1$-$C_2$-alkoxy-$C_1$-$C_2$-alkyl, cyano-$C_1$-$C_2$-alkyl, halogeno-$C_1$-$C_2$-alkyl, phenyl-$C_1$-$C_2$-alkyl, 1,3-dioxolan-2-yl-methyl, 2-methyl-1,3-dioxolan-4-yl-methyl, 2,2-dimethyl-1,3-dioxolan-4-yl-methyl or aminocarbonylmethyl, $R_2$ phenyl, mono- or disubstituted by halogen, methyl and/or methoxy, and $R_3$ $C_1$-$C_8$ alkyl, $C_2$-$C_8$ alkenyl, cyclopropyl or trichloromethyl, or $R_1$ is methyl or ethyl, $R_2$ α-cyanobenzyl or 1-cyano-2-phenylethyl and $R_3$ is ethyl.

The inventive compounds exhibit superior herbicidal properties when compared to the known anilides of the art as described above and thus improve the state of the art.

The herbicidal properties of these compounds include activity against a large number of undesired types of plants, while they exhibit selectivity towards culture plants.

As plants which can be controlled or fought, the following examples may be mentioned:

Gramineae
Festuca sp., Alopecurus sp., Agrostis sp., Avena sp., Echinochloa, Setaria sp., Sorghum sp., Poa sp., Lolium sp., Arrhenaterum sp., Phalaris sp., Phleum sp., Eleusine sp., Bromus sp., Hordeum sp. and others.
Cyperaceae
Cyperus sp. and others.
Liliaceae
Allium sp. and others.
Amaranthaceae
Amaranthus sp. and others.
Boraginaceae
Anchusa sp., Amsinckia sp., Myosotis sp. and others.
Caryophylaceae
Stellaria sp., Spergula sp., Cerastium sp. and others.
Chenopodiaceae
Chenopodium sp., Salsola kali, Atriplex sp., Kochia sp. and others.
Convolvulaceae
Ipomea sp. and others
Compositae
Ambrosia sp., Lactuca sp., Senecio sp., Xanthium sp., Galinsoga sp., Centaurea sp., Matricaria sp., Helianthus sp., Chrysanthemum sp., Cichorium intybus and others.
Cruciferae
Brassica sp., Cheiranthus cheiri, Capsella sp., Thlaspi sp., Sinapis sp. and others.
Euphorbiaceae
Euphorbia
Labiatae
Lamium sp., Galeopsis sp. and others.
Leguminosae
Medicago sp., Trifolium sp., Vicia sp., Cassia sp. and others.
Malvaceae
Abutilon theophrasti, Sida sp., Hibiscus sp., Anoda and others.
Papaveraceae
Papaver sp., Escholtzia and others.
Polygonacea
Polygonum sp. and others.
Portulacaceae
Portulaca sp. and others.
Rubiaceae
Galium sp., Richardia sp. and others.
Ranunculaceae
Delphinium sp., Adonis sp. and others.
Scrophulariaceae
Linaria sp., Digitalis sp., Veronica sp. and others.
Solanaceae
Datura sp., Solanum sp., Physalis sp. and others.
Urticaceae
Urtica sp. and others.
Umbelliferae
Daucus carota and others.

For fighting of the weeds, as a rule amount of 1 to 5 kg active agent/ha are used.

The use of the compositions may be either preemergent or postemergent. It is particularly of advantage that the inventive compounds are exceptionally compatible with agricultural cultures, in particular, potatoes, corn, rice, soy beans and wheat.

The inventive compounds can be used either alone, in mixture with one another or with other active agents. If desired, other defoliants, plant protection agents or pest control agents can be added for a particular purpose.

Insofar as a broadening of the activity spectrum is desired, other herbicides can be added. As examples of mixture partners, active agents such as triazines, aminotriazoles, anilides, diazines, uracils, aliphatic carboxylic acid and halogenated carboxylic acids, substituted benzoic acids and aryloxycarboxylic acids, and hydrazides, amides, nitriles and esters of such acids, carbamidic acids and thiocarbamidic acid esters, ureas, 2,3,6-trichlorobenzyloxypropanil, thiocyanogen-containing compounds and other additives.

As other additives should be understood as well non-phytotoxic additives, which may lead to synergistic increases in activity, such as wetting agents, emulsifiers, solvents and oily additives.

Advantageously the inventive active agents or mixtures thereof are applied in the form of preparations such as powders, granulates, solutions, emulsions or suspensions, with addition of liquid and/or solid carrier materials or thinners, and if desired with wetting agents, adhesives, emulsifiers and/or dispersants.

Suitable liquid carriers are for example water, aliphatic and aromatic hydrocarbons, such as benzene, toluene xylene, cyclohexanone, isophorone, dimethylsulfoxide, dimethylformamide, or mineral oil fractions.

As solid carrier materials are suitable mineral earths, such as tonsil, silica gel, talcum, kaolin, attaclay, calcite, and silica, and plant products, such as flours.

Surface active agents include calcium lignin sulfonate, polyoxyethylenealkyl phenol ether, naphthalene sulfonic acid and salts thereof, phenol sulfonic acids and salts thereof, formaldehyde condensates, fatty alcohol sulfates as well as substituted benzene sulfonic acids and salts thereof.

The amount of active agent(s) can vary within a wide range. For example, the compositions can contain about 10 to 80 weight-% active agent, about 90 to 20 weight-% liquid or solid carrier material as well as if desired up to 20 weight-% surface active agents.

The application of the compositions can be carried out in customary manner, for example with water as carrier in spray amounts of about 100 to 1000 liter/ha. An application of the agents in so-called low-volume- and ultra-low-volume processes is possible, as is application in the form of so-called microgranulates.

The novel compounds according to the invention may be prepared for example by a process in which a compound of the general formula

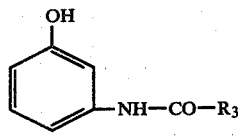

in the presence of organic bases, such as pyridine, or as alkali salts, such as sodium- or potassium salts, are reacted either with a compound of the general formula

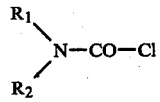

or with phosgene with addition of inorganic or organic bases, such as sodium hydroxide or dimethylaniline, to form the corresponding chloroformic acid of the general formula

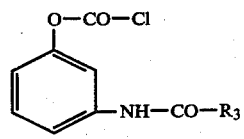

and this is then reacted with a compound of the formula

in the presence of bases, such as potassium carbonate, and the reaction product isolated in known manner.

As suitable solvents for these reactions may be mentioned ethyl acetate, acetonitrile, hexane, benzene, toluene, methylene chloride, carbon tetrachloride, tetrahydrofuran, dimethylformamide and other substances inert to the reaction.

The process in all reactions may be carried out at temperatures between about 0° and the boiling point of the solvent.

The hydroxyanilides used as starting material can be obtained in known manner through reaction of the corresponding acid chloride with m-aminophenol.

The following examples illustrate the preparation of the inventive compounds.

EXAMPLE 1

N-(2,2-diethylxyethyl)-carbanilic acid-[3-(2,2-dimethylvalerylamino)-phenyl]-ester To a solution of 20.9 g (0.1 Mol) N-(2,2-diethoxyethyl)-aniline in 50 ml ethyl acetate, a solution of 28.3 g (0.1 Mol) chloroformic acid-3-(2,2-dimethylvalerylamino)-phenyl ester and simultaneously a solution of 13.8 g (0.1 Mol) potassium carbonate in 70 ml water are added dropwise with stirring and cooling to 10°—15° C. The mixture is stirred 30 minutes at room temperature, the organic phase separated, thinned with a little ethyl acetate, washed at 0° with diluted hydrochloric acid and sodium chloride solutions, dried with magnesium sulfate, and the solvent distilled off under reduced pressure. The residue is recrystallized from ethyl acetate/pentane.

Yield: 36 g=79% of theory M.P.: 88°-89° C.

EXAMPLE 2

N-(2-cyanoethyl)-3-methylcarbanilic acid-[3-(trichloromethylcarbonylamino)-phenyl]-ester Into a solution of 16.0 g N-(2-cyanoethyl)-3-methylaniline in 100 ml acetonitrile, 31.7 g chloroformic acid-3-(trichloromethylcarbonylamino)-phenyl ester taken up in 100 ml acetonitrile is added dropwise. The reaction mixture is heated to boiling for another 10 minutes, cooled, stirred in 500 ml ice water, the precipitate filtered and recrystallized from isopropanol.

Yield: 31.5 g=72% theory M.P.: 118° C.

EXAMPLE 3

N-cyanomethylcarbanilic acid-[3-(tert.-butylcarbonylamino)phenyl]-ester

Into a solution of 13.2 g N-cyanomethylaniline in 150 ml acetonitrile is added 25.57 g chloroformic acid-[3-(tert.-butylcarbonylamino)-phenyl]-ester, then with further stirring 12.1 g N,N dimethylaniline is added dropwise and the mixture heated for an additional 15 minutes to boiling. The mixture is stirred after cooling in 1 l ice water, the substance which separates out is taken up and after drying in vacuum is recrystallized from a little acetonitrile.

Yield: 24.0 g=68% of theory M.P.: 173° C.

EXAMPLE 4

N-(2-cyanoethyl)-carbanilic acid-[3-(cyclopropylcarbonylamino)-phenyl]-ester 29.2 g N-(2-cyanoethyl)-aniline is dissolved in 200 ml acetonitrile and then reacted with 23.97 g chloroformic acid-[3-(cyclopropylcarbonylamino)-phenyl]-ester with stirring, with which the temperature of the solution rises to about 35° C. After standing overnight the solvent is removed under vacuum, the remaining oily residue is treated with water, the water is decanted and the oil brought to crystallization with a 1:1 mixture of isopropyl ether/isopropanol. The crystallizate is finally recrystallized from isopropanol.

Yield: 16.59 g=48% of theory M.P.: 142° C.

EXAMPLE 5

N-cyanomethyl-3-methylcarbanilic acid-[3-(propionylamino)phenyl]-ester

The potassium salt from 64.4 g (0.39 Mol) priopionic acid-3-hydroxyanilide is taken up in 300 ml acetonitrile. With addition by dropping of a solution of 81.4 g (0.39 Mol) N-cyanomethyl-N-(3-methylphenyl)-carbamoyl chloride in 250 ml acetonitrile with stirring, in five minutes the temperature rises from 28° to 44° C. Finally, the mixture is heated to reflux for 30 minutes. After evaporation of the solvent under reduced pressure, the residue is dissolved in ethyl acetate and water, washed at 0° with a little diluted sodium hydroxide, dried over magnesium sulfate and concentrated under reduced pressure. The oily residue is crystallized from ether.

Yield: 80.4 g=61% of theory M.P.: 97°–99° C.

In analogous manner the following compounds of the invention may be prepared.

| Name | Physical Constants |
| --- | --- |
| N—(2,2-dimethoxyethyl)-carbanilic acid-[3-(propionylamino)-phenyl]-ester | M.P.: 71–73° C. |
| N—cyanomethylcarbanilic acid-(3-propionylaminophenyl)-ester | M.P.: 130° C. |
| N—(2-cyanoethyl)-3-methylcarbanilic acid-(3-propionylaminophenyl)-ester | M.P.: 149–151° C. |
| N—(2-methoxyethyl)-carbanilic acid-[3-propionylamino)-phenyl]-ester | M.P.: 71–72° C. |
| N—(2-cyanoethyl)-4-methylcarbanilic acid-[3-propionylamino-phenyl]-ester | M.P.: 124–126° C. |
| N—(2-cyanoethyl)-2-methylcarbanilic acid-(3-propionylaminophenyl)-ester | M.P.: 120–122° C. |
| N—(2-methoxyethyl)-3-methylcarbanilic acid-(3-propionylaminophenyl)-ester | M.P.: 82–84° C. |
| N—(2,2-dimethoxyethyl)-4-methylcarbanilic acid-[3-(propionylamino)-phenyl]-ester | $n_D^{20}$: 1.5343 |
| N—(2,2-dimethoxyethyl)-3-methylcarbanilic acid-[3-(propionylamino)-phenyl]-ester | $n_D^{20}$: 1.5405 |
| N—(2-bromoethyl)-carbanilic acid-[3-(propionylamino)-phenyl]-ester | M.P.: 86–87° C. |
| N—(2-ethoxyethyl)-carbanilic acid-[3-(propionylamino)-phenyl]-ester | M.P.: 83–84° C. |
| N—(2-cyanoethyl)-carbanilic acid-[3-(propionylamino)-phenyl]-ester | M.P.: 126–128° C. |
| N—(2,2-dimethoxyethyl-2-methylcarbanilic acid-[3-(propinylamino)-phenyl]-ester | M.P.: 105–107° C. |
| N—(1-cyano-2-phenylethyl)-N—methyl-carbaminic acid-[3-(propionylamino)-phenyl]-ester | M.P.: 104° C. |
| N—(α-cyanobenzyl)-N—ethylcarbaminic acid-[3-(propionylamino)-phenyl]-ester | M.P.: 76° C. |
| N—(2-cyanoethyl)-3-methylcarbanilic acid-[3-(tert.-butylcarbonylamino)-phenyl]-ester | M.P.: 122° C. |
| N—(2-cyanoethyl)-carbanilic acid-[3-(tert.-butylcarbonylamino)-phenyl]-ester | M.P.: 118° C. |
| N—(1,3-dioxolan-2-yl-methyl)-carbanilic acid-[3-(propionylamino)-phenyl]-ester | M.P.: 98–99° C. |
| 3-methoxy-N—(2-methoxyethyl)-carbanilic acid-[3-(propionylamino)-phenyl]-ester | $n_D^{20}$: 1.5614 |
| N—(4-methyl-1,3-dioxolan-2-yl-methyl)-carbanilic acid-[3-(propionylamino)-phenyl]-ester | $n_D^{20}$: 1.5559 |
| N—cyanomethylcarbanilic acid-[3-(2,2-dimethylvalerylamino)-phenyl]-ester | M.P.: 152–153° C. |
| N—(2-cyanoethyl)-carbanilic acid-[3-(2,2-dimethylvalerylamino)-phenyl]-ester | M.P.: 93–95° C. |
| N—(2-cyanoethyl)-carbanilic acid-[3-(2-methylpropionylamino)-phenyl]-ester | M.P.: 136–137° C. |
| N—(2-chloroethyl)-carbanilic acid-[3-(2,2-dimethylvalerylamino)-phenyl]-ester | M.P.: 101–102.5° C. |
| N—(2-chloroethyl)-carbanilic acid-[3-(propionylamino)-phenyl]-ester | M.P.: 107–109° C. |
| N—(2-phenylethyl)-carbanilic acid-[3-(propionylamino)-phenyl]-ester | M.P.: 93–94° C. |
| N—(2-cyanoethyl)-carbanilic acid-[3-(crotonoylamino)-phenyl]-ester | M.P.: 117–119° C. |
| N—(2-chloroethyl)-carbanilic acid-[3-(crotonoylamino)-phenyl]-ester | M.P.: 131–133° C. |
| N—(2,2-dimethoxyethyl)-carbanilic acid-[3-(2,2-dimethylvalerylamino)-phenyl]-ester | M.P.: 77–79° C. |
| N—(aminocarbonylmethyl)-carbanilic acid-[3-(cyclopropylcarbonylamino)-phenyl]-ester | M.P.: 197° C. |
| N—(2-aminocarbonylethyl)-carbanilic acid-[3-(cyclopropylcarbonylamino)-phenyl]-ester | M.P.: 166° C. |
| N—(2-cyanoethyl)-3-methylcarbanilic acid-[3-(cyclopropylcarbonylamino)-phenyl]-ester | M.P.: 175° C. |
| N—cyanomethylcarbanilic acid-[3-(trichloromethylcarbonylamino)-phenyl]-ester | M.P.: 102° C. |
| N—(2-cyanoethyl)-carbanilic acid-[3-(trichloromethylcarbonylamino)-phenyl]-ester | M.P.: 137° C. |
| N—(2-methoxyethyl)-carbanilic acid-[3-(tert.-butylcarbonylamino)-phenyl]-ester | $n_D^{20}$: 1.5509 |
| N—(2-methoxyethyl)-3-methoxycarbanilic acid-[3-(tert.-butylcarbonylamino)-phenyl]-ester | $n_D^{20}$: 1.5482 |
| N—(2-methoxyethyl)-carbanilic acid-[3-(cyclopropylcarbonylamino)-phenyl]-ester | M.P.: 133° C. |
| N—(2-methoxyethyl)-carbanilic acid-[3-(trichloromethylcarbonylamino)-phenyl]-ester | $n_D^{20}$: 1.5804 |
| N—(2-methoxyethyl)-3-methoxycarbanilic acid-[3-(trichloromethylcarbonylamino)-phenyl]-ester | M.P.: 135° C. |
| N—(2,2-dimethyl-1,3-dioxolan-4-yl-methyl)-carbanilic acid-[3-(2,2-dimethylvalerylamino)-phenyl]-ester | M.P.: 100–102° C. |
| N—(2-ethoxyethyl)-carbanilic acid-[3-(cyclopropylcarbonylamino)-phenyl]-ester | M.P.: 109° C. |
| N—cyanomethyl-3-chlorocarbanilic acid-[3-(trichloromethylcarbonylamino)-phenyl]-ester | M.P.: 162° C. |
| N—(2,2-dimethoxyethyl)-3-methylcarbanilic acid-[3-(tert.-butylcarbonylamino)-phenyl]-ester | viscous oil |
| N—(2-hydroxyethyl)-carbanilic acid-[3-(cyclopropylcarbonylamino)-phenyl]-ester | M.P.: 116–117° C. |
| N—(2-methoxyethyl)-4-fluorocarbanilic acid-[3-cyclopropylcarbonylamino)-phenyl]-ester | M.P.: 103–105° C. |
| N—(2-ethoxyethyl)-4-fluorocarbanilic acid-[3-(cyclopropylcarbonylamino)-phenyl]-ester | M.P.: 77–79° C. |

The inventive compounds are color and odorless crystalline or oily substances, and are well-soluble in acetone, dimethylformamide, isophorone, cyclohexanone, tetrahydrofuran and dimethylsulfoxide.

The following serve to illustrate the preparation of starting materials.

(a) 2,2-dimethylvalerianic acid-3-hydroxyanilide

Into a solution of 327 g (3 Mol) m-aminophenol in about 1 l ethyl acetate after addition of 400 ml water and 76 g magnesium oxide, 445 g (3 Mol) 2,2-dimethylvalerianic acid chloride is added dropwise with stirring, during which the temperature is kept between 10°–20° through cooling. The mixture is then stirred for 1 hour at room temperature. 400 ml concentrated hydrochloric acid is added dropwise at 0°–5° and the mixture stirred for 10 minutes. The organic phase is separated off, washed to neutrality with sodium chloride solution and dried over magnesium sulfate. The ethyl acetate is distilled off in part and the residue mixed with pentane, from which the reaction product crystallizes out.

Yield: 550 g=83% of theory M.P.: 155°–156° C.

Analogously are prepared:

Propionic acid-3-hydroxyanilide M.P.: 183°–185° C.

2-methylpropionic acid-3-hydroxyanilide M.P.: 180° C.

Crotonic acid-3-hydroxyanilide M.P.: 158°–159° C.

(b) Chloroformic acid-3-(propionylamino)-phenyl ester

A solution of 177 ml phosgene in 700 ml ethyl acetate is reacted with 292 g (1.77 Mol) propionic acid-3-hydroxyanilide. With stirring and cooling to 10°–15° a solution of 225 ml (1.77 Mol) N,N-dimethylaniline in 300 m. ethyl acetate is added dropwise. The mixture is stirred for 30 minutes at 50° C. The solution cooled to 10° C. is poured over ice, stirred for about 10 minutes, the organic phase separated off, washed with NaCl solution, dried over magnesium sulfate and concentrated under reduced pressure. The residue crystallizes upon addition of 600 ml pentane.

Yield: 327 g–81% of theory
M.P.: 72°–73° C.

Analogously are obtained:

Chloroformic acid-3-(2-methylpropionylamino)-phenyl ester M.P.: 69°–71° C.

Chloroformic acid-3-(crotonylamino)-phenyl ester $n_D^{20}$: 1.5327

Chloroformic acid-3-(2,2-dimethylvaleroylamino)-phenyl ester $n_D^{20}$: 1.5273

(c) Chloroformic acid-[3-(cyclopropylcarbonylamino)-phenyl]ester 100 ml phosgene is concentrated at −20° C., taken up in 1 l ethyl acetate and at 0° C. with stirring is reacted with 177.2 g cyclopropanecarboxylic acid-3-hydroxyanilide with a melting point of 184° C. Into this reaction mixture with further cooling is added dropwise 121 g N,N-dimethylaniline. Finally, the mixture is stirred for another hour at 40° C., the excess phosgene removed by a stream of nitrogen gas, the mixture cooled to room temperature and the ethyl acetate phase extracted twice with 250 ml ice water. After separation of the organic phase, it is dried over magnesium sulfate, the solvent distilled under vacuum and the obtained residue brought to crystallization by addition of petroleum ether. One obtains 207 g (86% of theory) of the above-noted substance with a melting point of 94° C.

One may prepare in an analogous manner the following:

chloroformic acid-[3-(tert.-butylcarbonylamino)-phenyl]-ester M.P.: 75° C.

Chloroformic acid-[3-(trichloromethylcarbonylamino)-phenyl]-ester $n_D^{20}$: 1.5786

The following examples serve to illustrate the use of the inventive compounds and their underlying herbicidal activity.

EXAMPLE 6

In a greenhouse the compounds listed in the table were sprayed over Solanum and Brassica as test plants in postemergence tests in an amount of 5 kg active agent/ha, dissolved in 500 liters water/ha. Three weeks after treatment the results are determined, whereby 0=no effect and 4=total destruction. As can be seen from the table, as a rule there was a total destruction of the test plants.

| Compounds of the Invention | Brassica | Solanum |
| --- | --- | --- |
| N—(2,2-dimethoxyethyl)-carbanilic acid-[3-(propionylamino)-phenyl]-ester | 4 | 4 |
| N—cyanomethylcarbanilic acid-[3-(propionylamino)-phenyl]-ester | 4 | 4 |
| N—(2-cyanoethyl)-3-methylcarbanilic acid-[3-(propionylamino)-phenyl]-ester | 4 | 4 |
| N—methoxyethylcarbanilic acid-[3-(propionylamino)-phenyl]-ester | 4 | 4 |
| N—(2-cyanoethyl)-4-methylcarbanilic acid-[3-(propionylamino)-phenyl]-ester | 4 | 4 |
| N—(2-cyanoethyl)-4-methylcarbanilic acid-[3-(propionylamino)-phenyl]-ester | 4 | 4 |
| N—(2-methoxyethyl)-3-methylcarbanilic acid-[3-(propionylamino)-phenyl]-ester | 4 | 4 |
| N—(2,2-dimethoxyethyl)-4-methylcarbanilic acid-[3-(propionylamino)-phenyl]-ester | 4 | 4 |
| N—(2,2-dimethoxyethyl)-3-methylcarbanilic acid-[3-(propionylamino)-phenyl]-ester | 4 | 4 |
| N—(2-bromoethyl)-carbanilic acid-[3-(propionylamino)-phenyl]-ester | 4 | 4 |
| N—(2-ethoxyethyl)-carbanilic acid-[3-(propionylamino)-phenyl]-ester | 4 | 4 |
| N—(2-cyanoethyl)-carbanilic acid-[3-(propionylamino)-phenyl]-ester | 4 | 4 |
| N—(2,2-dimethoxyethyl-2-methylcarbanilic acid-[3-(propionylamino)-phenyl]-ester | 4 | 4 |
| N—cyanomethyl-3-methylcarbanilic acid-[3-(propionylamino)-phenyl]-ester | 4 | 4 |
| N—(1-cyano-2-phenyl-ethyl)-N—methyl-carbaminic acid-[3-(propionylamino)-phenyl]-ester | 4 | 4 |
| N—(α-cyano-benzyl)-N—ethyl-carbaminic acid-[3-(propionylamino)-phenyl]-ester | 4 | 4 |
| N—(1,3-dioxolan-2-yl-methyl)-carbanilic acid-[3-(propionylamino)-phenyl]-ester | 4 | 4 |
| 3-methoxy-N—(2-methoxyethyl)-carbanilic acid-[3-(propionylamino)-phenyl]-ester | 4 | 4 |
| N—(4-methyl-1,3-dioxolan-2-yl-methyl)-carbanilic acid-[3-(ethylcarbonylamino)-phenyl]-ester | 4 | 4 |
| N—cyanomethylcarbanilic acid-[3-(2,2-dimethylvalerylamino)-phenyl]-ester | 4 | 4 |
| N—(2-cyanoethyl)-carbanilic acid-[3-(2,2-dimethylvalerylamino)-phenyl]-ester | 4 | 4 |
| N—(2-cyanoethyl)-carbanilic acid-[3-(2-methylpropionylamino)-phenyl]-ester | 4 | 4 |
| N—(2,2-diethoxyethyl)-carbanilic acid-[3-(2,2-dimethylvalerylamino)-phenyl]-ester | 4 | 4 |
| N—(2-chloroethyl)-carbanilic acid-[3-(2,2-dimethylvalerylamino)-phenyl]-ester | 4 | 4 |
| N—(2-chloroethyl)-carbanilic acid-[3-(propionylamino)-phenyl]-ester | 4 | 4 |
| N—(2-phenylethyl)-carbanilic acid-[3-(propionylamino)-phenyl]-ester | 4 | 4 |
| N—(2-cyanoethyl)-carbanilic acid-[3-(crotonoylamino)-phenyl]-ester | 4 | 4 |
| N—(2-chloroethyl)-carbanilic acid-[3-(crotonoylamino)-phenyl]-ester | 4 | 4 |
| N—(2,2-dimethoxyethyl)-carbanilic acid-[3-(2,2-dimethylvalerylamino)-phenyl]-ester | 4 | 4 |
| N—(2-cyanoethyl)-carbanilic acid-[3-(cyclopropylcarbonylamino)-phenyl]-ester | 4 | 4 |
| N—cyanomethyl-carbanilic acid-[3-(tert.-butylcarbonylamino)-phenyl]-ester | 4 | 4 |
| N—(2-cyanoethyl)-3-methyl-carbanilic acid-[3-(tert.-butylcarbonylamino)-phenyl]-ester | 4 | 4 |
| N—(2-cyanoethyl)-carbanilic acid-[3-(tert.-butylcarbonylamino)-phenyl]-ester | 4 | 4 |
| N—cyanomethylcarbanilic acid-[3-(trichloro- | | |

-continued

| Compounds of the Invention | Brassica | Solanum |
|---|---|---|
| methylcarbonylamino)-phenyl]-ester | | |
| N—(2-methoxyethyl)-carbanilic acid-[3-(tert.-butylcarbonylamino)-phenyl]-ester | 4 | 4 |
| N—(2-methoxyethyl)-3-methoxy-carbanilic acid-[3-(tert.-butylcarbonylamino)-phenyl]-ester | 4 | 4 |
| N—(2-methoxyethyl)-carbanilic acid-[3-(cyclopropylcarbonylamino)-phenyl]-ester | 4 | 4 |
| N—(2-methoxyethyl)-carbanilic acid-[3-(trichloromethylcarbonylamino)-phenyl]-ester | 4 | 4 |
| N—(2-methoxyethyl)-3-methoxy-carbanilic acid-[3-(trichloromethylcarbonylamino)-phenyl]-ester | 4 | 4 |
| N—(2-ethoxyethyl)-carbanilic acid-[3-(cyclopropylcarbonylamino)-phenyl]-ester | 4 | 4 |
| N—(2-hydroxyethyl)-carbanilic acid-[3-(cyclopropylcarbonylamino)-phenyl]-ester | 4 | 4 |
| N—(2-methoxyethyl)-4-fluorocarbanilic acid-[3-(cyclopropylcarbonylamino)-phenyl]-ester | 4 | 4 |
| N—(2-ethoxyethyl)-4-fluorocarbanilic acid-[3-(cyclopropylcarbonylamino)-phenyl]-ester | 4 | 4 |
| N—cyanomethyl-3-chlorocarbanilic acid-[3-(trichloromethylcarbonylamino)-phenyl]-ester | 4 | 4 |
| N—(2,2-dimethoxyethyl)-3-methylcarbanilic acid-[3-(tert.-butylcarbonylamino)-phenyl]-ester | 4 | 4 |
| Untreated | 0 | 0 |

EXAMPLE 7

In a greenhouse the plants in the table were treated postemergently with the compounds listed in an amount of 3 kg active agent/ha. To this end, the agent was sprayed uniformly over the plants. The evaluation followed, in which 0=totally destroyed and 10=no damage. Three weeks after treatment the inventive compounds show a high selectivity with exceptional activity against the weeds. The comparison compound does not exhibit this selectivity.

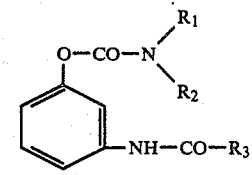

wherein
  $R_1$ is cyano-$C_1$-$C_2$-alkyl;
  $R_2$ is phenyl optionally mono- or disubstituted by one or more substituents selected from the group consisting of halogen, methyl and methoxy; and
  $R_3$ is $C_1$–$C_8$ alkyl, $C_2$–$C_8$ alkenyl, cyclopropyl or trichloromethyl, or $R_1$ is methyl or ethyl, $R_2$ is α-cyanobenzyl or 1-cyano-2-phenylethyl and $R_3$ is ethyl.

2. A compound as defined in claim 1, which is N-(2-cyanoethyl)-3-methylcarbanilic acid-[3-(trichloromethylcarbonylamino)-phenyl]-ester.

3. A compound as defined in claim 1, which is N-cyanomethylcarbanilic acid-[3-(tert.-butylcarbonylamino)-phenyl]-ester.

4. A compound as defined in claim 1, which is N-(2-cyanoethyl)-carbanilic acid-[3-(cyclopropylcarbonylamino)-phenyl]-ester.

5. A compound as defined in claim 1, which is N-cyanomethylcarbanilic acid-[3-(propionylamino)-phenyl]-ester.

6. A compound as defined in claim 1, which is N-(2-cyanoethyl)-4-methylcarbanilic acid-[3-(propionylamino)-phenyl]-ester.

7. A compound as defined in claim 1, which is N-(2-cyanoethyl)-2-methylcarbanilic acid-[3-(propionylamino)-phenyl]-ester.

8. A compound as defined in claim 1, which is N-(2-cyanoethyl)-carbanilic acid-[3-(propionylamino)-phenyl]-ester.

| | Sugar beets | Potatoes | Cotton | Soy beans | Rice | Gypsophyla sp. | Solanum sp. | Phacelia | Ipomoea sp. | Lamium sp. | Setaria sp. | Brassica sp. |
|---|---|---|---|---|---|---|---|---|---|---|---|---|
| Inventive Composition | | | | | | | | | | | | |
| N—(2-cyanoethyl)-3-methylcarbanilic acid-[3-(propionylamino)-phenyl]-ester | — | 10 | 10 | 10 | 10 | 0 | 0 | 0 | 0 | 0 | 0 | 0 |
| N—(2-methoxyethyl)-3-methylcarbanilic acid-[3-(propionylamino)-phenyl]-ester | 10 | 10 | 10 | 10 | 10 | 0 | 0 | 0 | 0 | 0 | 0 | 0 |
| N—cyanomethyl-3-methylcarbanilic acid-[3-(propionylamino)-phenyl]-ester | 10 | 10 | 10 | 10 | 10 | 0 | 0 | 0 | 0 | 0 | 0 | 0 |
| N—(α-cyanobenzyl)-N—ethylcarbaminic acid-[3-(propionylamino)-phenyl]-ester | 10 | 10 | 10 | 10 | 10 | 0 | 0 | 0 | 0 | 0 | 0 | 0 |
| N—(2-chloroethyl)-carbanilic acid-[3-(2,2-dimethylvalerylamino)-phenyl]-ester | 10 | 10 | 10 | 10 | 10 | 0 | 0 | 0 | 0 | 0 | 0 | 0 |
| Comparison Composition (from BE-PS 686 239) | | | | | | | | | | | | |
| N—butylcarbaminic acid-[3-(propionylamino)-phenyl]-ester | 0 | 5 | 0 | 1 | 5 | 0 | 0 | 0 | 0 | 0 | 0 | 0 |
| Isobutylcarbaminic acid-[3-(propionylamino)-phenyl]-ester | 0 | 8 | 0 | 1 | 8 | 0 | 0 | 0 | 0 | 0 | 0 | 0 |

Without further analysis, the foregoing will so fully reveal the gist of the present invention that others can by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compound of the formula

9. A compound as defined in claim 1, which is N-cyanomethyl-3-methylcarbanilic acid-[3-(propionylamino)-phenyl]-ester.

10. A compound as defined in claim 1, which is N-(1-cyano-2-phenyl-ethyl)-N-methyl-carbaminic acid-[3-(propionylamino)-phenyl]-ester.

11. A compound as defined in claim 1, which is N-(α-cyano-benzyl)-N-ethylcarbaminic acid-[3-(propionylamino)-phenyl]-ester.

12. A compound as defined in claim 1, which is N-cyanomethylcarbanilic acid-[3-(2,2-dimethylvalerylamino)-phenyl]-ester.

13. A compound as defined in claim 1, which is N-(2-cyanoethyl)-carbanilic acid-[3-(2,2-dimethylvalerylamino)-phenyl]-ester.

14. A compound as defined in claim 1, which is N-(2-cyanoethyl)-carbanilic acid-[3-(2-methylpropionylamino)-phenyl]-ester.

15. A compound as defined in claim 1, which is N-(2-cyanoethyl)-carbanilic acid-[3-(crotonoylamino)-phenyl]-ester.

16. A compound as defined in claim 1, which is N-(2-cyanoethyl)-3-methylcarbanilic acid-[3-(cyclopropylcarbonylamino)-phenyl]-ester.

17. A compound as defined in claim 1, which is N-(2-cyanoethyl)-3-methylcarbanilic acid-[3-(tert.-butylcarbonylamino)-phenyl]-ester.

18. A compound as defined in claim 1, which is N-(2-cyanoethyl)-carbanilic acid-[3-(tert.-butylcarbonylamino)-phenyl]-ester.

19. A compound as defined in claim 1, which is N-cyanomethylcarbanilic acid-[3-(trichloromethylcarbonylamino)-phenyl]-ester.

20. A compound as defined in claim 1, which is N-(2-cyanoethyl)-carbanilic acid-[3-(trichloromethylcarbonylamino)-phenyl]-ester.

21. A compound as defined in claim 1, which is N-cyanomethyl-3-chlorocarbanilic acid-[3-(trichloromethylcarbonylamino)-phenyl]-ester.

22. A herbicidal composition containing a herbicidally effective amount of at least one compound as described in claim 1, further comprising carrier material.

23. A composition as defined in claim 22, further comprising carrier material and optionally containing other additives.

* * * * *